United States Patent
Pond

(10) Patent No.: US 6,319,002 B1
(45) Date of Patent: Nov. 20, 2001

(54) HANDHELD DEVICE FOR APPLYING DENTAL MATERIALS

(76) Inventor: Gary J. Pond, 2816 N. Main St., Racine, WI (US) 53402

(*) Notice: Subject to any disclaimer, the term of this patent is extended or adjusted under 35 U.S.C. 154(b) by 0 days.

(21) Appl. No.: 09/648,398

(22) Filed: Aug. 24, 2000

(51) Int. Cl.$^7$ .................................................. A61C 5/04
(52) U.S. Cl. ............................................. 433/89; 433/90
(58) Field of Search .................... 433/80, 81, 89, 433/90; 222/390

(56) References Cited

U.S. PATENT DOCUMENTS

| | | | |
|---|---|---|---|
| D. 224,655 | 8/1972 | Dragan | D24/99 |
| D. 289,682 | 5/1987 | Dragan | D24/16 |
| D. 292,825 | 11/1987 | Dragan | D24/16 |
| D. 315,956 | 4/1991 | Dragan | D24/14 |
| D. 320,852 | 10/1991 | Drumm | D24/114 |
| D. 334,803 | 4/1993 | Discko, Jr. | D24/112 |
| D. 353,673 | 12/1994 | Discko et al. | D24/152 |
| D. 359,119 | 6/1995 | Dragan et al. | D24/114 |
| 2,381,785 | 8/1945 | Thompson | 433/90 |
| 2,812,765 | 11/1957 | Tofflemire | 433/80 |
| 3,164,153 | 1/1965 | Zorzi | 433/88 |
| 3,208,145 | 9/1965 | Turner | 433/80 |
| 3,581,399 | 6/1971 | Dragan | 433/90 |
| 3,593,423 | 7/1971 | Jones et al. | 433/80 |
| 3,624,907 | 12/1971 | Brass et al. | 433/80 |
| 3,727,310 | 4/1973 | Baker | 433/80 |
| 3,900,954 | 8/1975 | Dragan | 433/90 |
| 4,019,654 * | 4/1977 | van Manen | 222/390 |
| 4,138,816 * | 2/1979 | Warden et al. | 433/90 |
| 4,215,476 | 8/1980 | Armstrong | 433/80 |
| 4,340,365 | 7/1982 | Pisanu | 433/80 |
| 4,397,640 | 8/1983 | Haug et al. | 433/95 |
| 4,526,573 | 7/1985 | Lester et al. | 433/95 |
| 4,569,662 * | 2/1986 | Dragan | 433/89 |
| 4,680,026 | 7/1987 | Weightman et al. | 433/84 |
| 4,682,950 | 7/1987 | Dragan | 433/90 |
| 4,684,344 * | 8/1987 | Brockway et al. | 433/81 |
| 4,767,326 | 8/1988 | Bennett et al. | 433/90 |
| 4,768,954 | 9/1988 | Dragan | 433/90 |
| 4,872,837 | 10/1989 | Issalene et al. | 433/80 |
| 4,963,093 | 10/1990 | Dragan | 433/90 |
| 4,969,816 | 11/1990 | Drumm | 433/90 |
| 5,052,927 | 10/1991 | Discko, Jr. | 433/90 |
| 5,061,179 | 10/1991 | Dragan | 433/90 |
| 5,061,180 | 10/1991 | Wiele | 433/91 |
| 5,083,921 | 1/1992 | Dragan | 433/90 |

(List continued on next page.)

FOREIGN PATENT DOCUMENTS

| | | |
|---|---|---|
| 197 00 480 A1 | 7/1998 | (DE) . |
| WO 98/29054 | 7/1998 | (WO) . |

OTHER PUBLICATIONS

Infodent International (p.13) Magazine Ad Saremco SR–J Tip Applicator Date currently not available.

Primary Examiner—John J. Wilson
(74) Attorney, Agent, or Firm—Ryan Kromholz & Manion S.C.

(57) ABSTRACT

A dental handpiece arranged to be coupled to a capsule containing a composite material and for delivering and/or retracting the composite material to and from the mouth of a patient. The handpiece includes an elongate tubular member having a hollow chamber for receiving a reversible electric motor, a battery for supplying electric power to the motor and a drive shaft coupled to the motor. The drive shaft is restrained from longitudinal movement but contains a threaded portion for engagement with a threaded bore of a longitudinally movable plunger. The plunger is arranged to force outward movement of the composite material from the reservoir of the capsule. A manually operated electric switch is preferably mounted in the wall of the handpiece with a portion extending internally and externally of the wall.

4 Claims, 8 Drawing Sheets

U.S. PATENT DOCUMENTS

| | | | |
|---|---|---|---|
| 5,122,057 | 6/1992 | Discko, Jr. | 433/90 |
| 5,129,825 | 7/1992 | Discko | 433/90 |
| 5,165,890 | 11/1992 | Discko, Jr. | 433/90 |
| 5,171,146 | 12/1992 | Guerci | 433/81 |
| 5,172,807 | 12/1992 | Dragan et al. | 206/219 |
| 5,306,147 | 4/1994 | Dragan et al. | 433/90 |
| 5,336,088 | 8/1994 | Discko, Jr. | 433/90 |
| 5,468,148 | 11/1995 | Ricks | 433/80 |
| 5,474,450 | 12/1995 | Chronister | 433/80 |
| 5,658,144 | 8/1997 | Tinder et al. | 433/80 |
| 5,716,210 | 2/1998 | Novak | 433/82 |
| 5,772,433 | 6/1998 | Esrock | 433/80 |
| 5,899,692 | 5/1999 | Davis et al. | 433/80 |
| 6,056,165 * | 5/2000 | Speranza | 222/390 |
| 6,093,020 | 7/2000 | Pond et al. | 433/80 |

\* cited by examiner

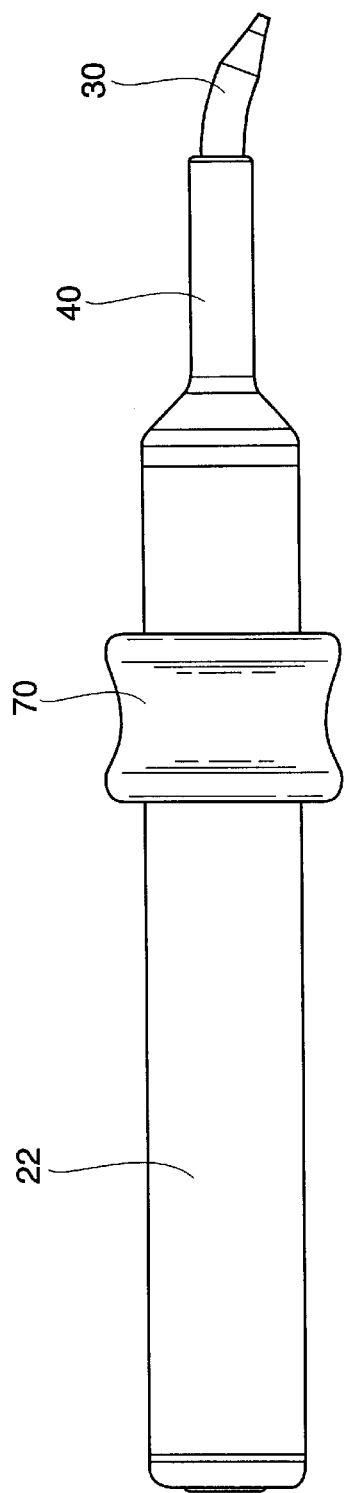
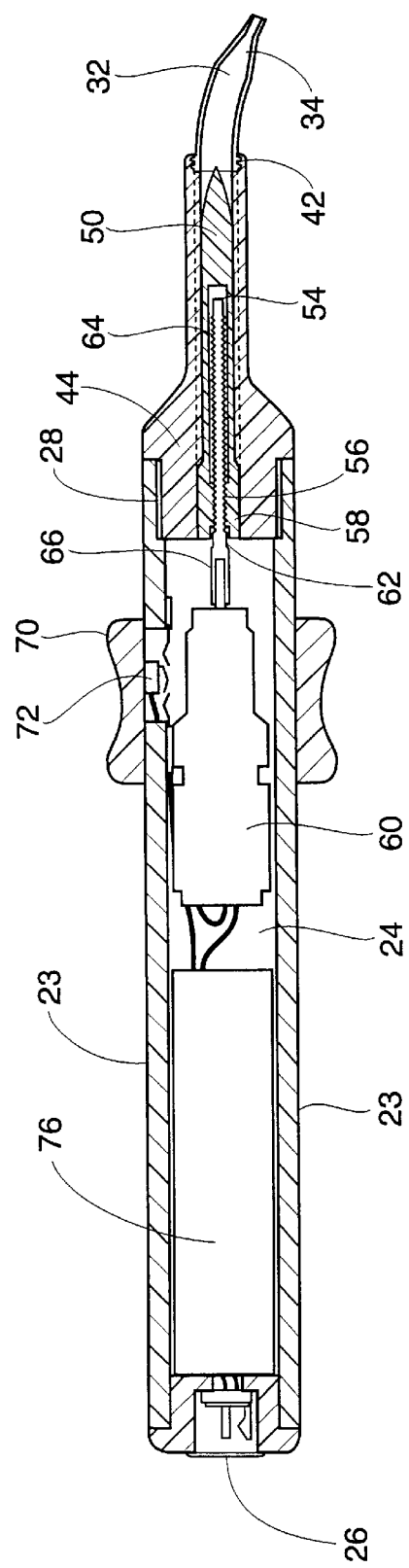
Fig. 3
Fig. 4

HANDHELD DEVICE FOR APPLYING DENTAL MATERIALS

BACKGROUND OF THE INVENTION

The present invention relates generally to a syringe and capsule therefore, and more specifically to a dental placement syringe and disposable capsule for use therewith.

Dental syringes and disposable plastic capsules for dispensing dental material are well known in the art. Disposable capsules, such as those described in U.S. Pat. Nos. 4,969,816; 5,165,890; 5,172,807; 5,306,147; and 5,336,088, are available in a number of sizes and shapes for dispensing a variety of dental materials. They essentially comprise a plastic body having an internal reservoir, a large diameter opening on one end and a small diameter discharge tip on the opposite end, as well as a separate piston or plug inserted into the large opening.

The internal reservoir is filled with dental material, and the plug seals the material within the reservoir. As the plug is pushed deeper into the reservoir, dental material is dispensed from the discharge tip. The capsules may be preloaded with dental material, or may be loaded on site as needed.

Dental syringes, such as those described in U.S. Pat. Nos. 5,061,179; 5,306,147; and 5,336,088, hold the disposable capsules in place, and have a longitudinally moving plunger that can push the plug into the reservoir, dispensing the dental material in a controlled fashion.

The longitudinally moving plunger is typically moved by squeezing or compressing a spring loaded handle or plunger. A full compression of the handle results in all the dental material being dispensed.

Although dental syringes and disposable capsules have become a convenient way to dispense a controlled amount of dental material into a patient's mouth, the size and shape of existing syringes can cause inconvenience. Syringes that are thin and fit easily into a patient's mouth, such as described in U.S. Pat. No. 5,129,825, must be held like a conventional manually operated syringe, using two fingers and the thumb to hold the device, with the thumb depressing the plunger. Positioning the hand with the thumb and fingers spread is uncomfortable and can quickly become tiresome. Holding the syringe by its rear portions also creates difficulty in controlling the exact location of the capsule tip and placement of the dental material.

Pistol grip syringes, such as described in U.S. Pat. No. 5,061,179, are more comfortable for the dentist's hand and can allow more precise placement of the dental material, but are bulky and difficult to fit in the small confines of an oral cavity.

Another difficulty in using conventional syringes is that once the dental material is dispensed, it cannot be drawn back into the reservoir. If too much material has been dispensed, the dentist must use another tool to pick up the excess. This is because the syringe's longitudinally moving plunger can only push the plug deeper into the reservoir. After an amount of material is dispensed, releasing the handle will allow the handle and longitudinally moving aperture to return to their original positions, but the plug will be left in the farthest forward position inside the capsule tip.

For the foregoing reasons, there is a need for a device that will allow a dentist to precisely dispense, and possibly recollect, a controlled amount of dental material into a patient's mouth in a manner that is comfortable for both the dentist and the patient.

SUMMARY OF THE INVENTION

The present invention is directed to a dental handpiece that satisfies the needs described above. The present invention preferably comprises a body with a hollow chamber, a reversible electric motor, a power supply, a retractable plunger, a drive shaft, a manual power switch, a removable nose cone and a disposable capsule tip.

The body of the handpiece is designed to fit comfortably in the dentist's hand, similar to the fit of a highlighting marker or soldering iron. Power is controlled by a sliding switch that normally rests in a neutral position and can move forward or backward, thus powering the electric motor in either forward or reverse operation. The sliding portion of the switch may be a ring that encircles the main shaft of the handpiece, allowing convenient switching operation by either the thumb, a finger, or both working simultaneously.

The hollow chamber of the handpiece holds the electric motor, rechargeable battery and drive shaft. The motor rotates the drive shaft, which is threaded and axially fixed. The retractable plunger tapers to a point at the front end, and has an internal longitudinal bore beginning at the rearward end and spanning most of its length. A portion of the longitudinal bore is threaded, and engages the threaded drive shaft. As the fixed drive shaft rotates in one direction, or the other, the plunger either advances or retracts longitudinally.

The detachable nose cone connects to the body and holds a disposable capsule tip filled with dental material. As the plunger advances forward, the tapered end enters the internal reservoir of the capsule tip, thus dispensing the material. The plunger is made of a somewhat flexible material that can bend around a curve in the capsule tip, but can still withstand high temperature sterilization. Because the plunger is retractable, and no separate insert plug is used, the device has the ability to draw excess material back into the capsule tip.

The overall shape of the device allows for precise control while comfortably fitting in the dentist's hand and the patient's mouth. The electric dispensing mechanism, as opposed to conventional manual operation, generates the same result with less physical effort, and allows greater precision and less fatigue during extended use. The tapered plunger reduces waste by eliminating the need for a separate disposable plug, and allows the device to recollect unneeded dental material if an excess is dispensed. The detachable nose cone and the plunger can be removed, sterilized, and reused. The present invention can also be connected to a battery charger without disassembly.

DESCRIPTION OF THE DRAWINGS

FIG. 3 is a side elevational view of the present embodiment of the invention.

FIG. 4 is a longitudinal sectional view of FIG. 3.

DETAILED DESCRIPTION

Figure 1:
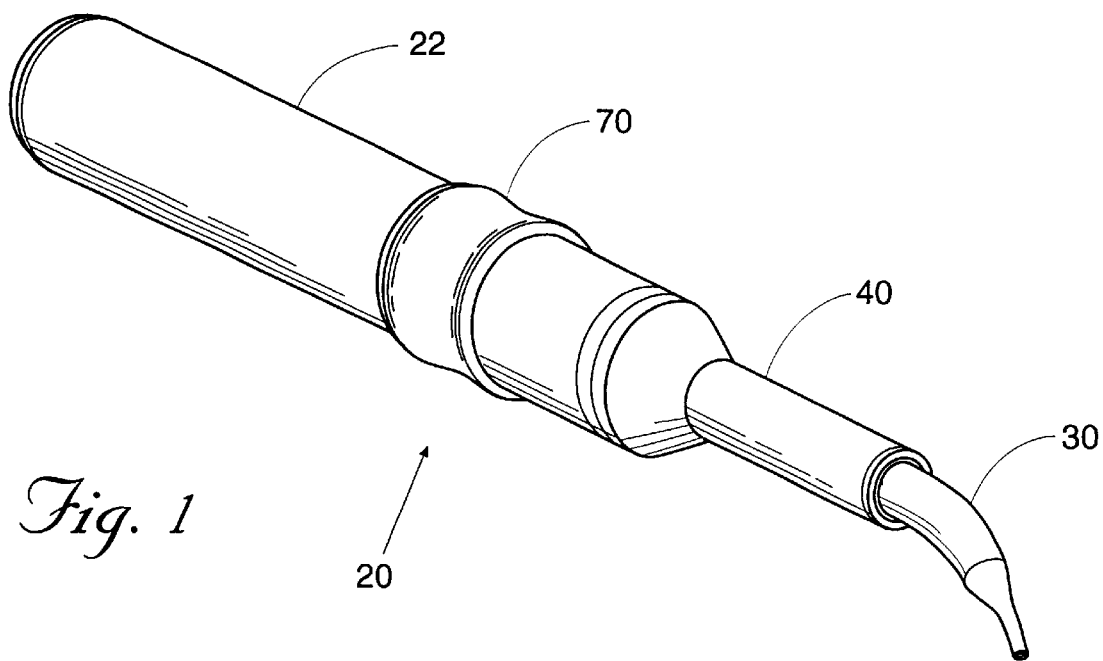
FIG. 1 is a perspective view of the present embodiment of the handpiece of this invention.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Referring to FIGS. 1, 2, 3 and 4, an embodiment of a dental handpiece 20 capable of dispensing and recollecting a controlled amount of dental material is disclosed. The dental handpiece 20 includes a main body 22, a manually operated power switch 70, a detachable nose cone 40, and a disposable capsule tip 30. The main body 22 has an outer wall 23, an end cap 26 and a hollow internal chamber 24 that contains a battery 76, a reversible electric motor 60, a drive shaft 62 and an extendable plunger 50 (see FIG. 4). The battery 76 may be rechargeable, and the main body 22 may include an external electrical connection 27 for recharging the battery when the handpiece is not in use.

The manually operated power switch 70 controls an electrical connection 72 between the battery 76 and electric motor 60. In the preferred embodiment of FIG. 4, inclusive, the switch 70 takes the form of a sliding ring encircling a portion of the main body 22. The switch 70 is shown in FIG. 4 normally resting in a neutral position, wherein the electrical connection 72 is open. Sliding the switch forward or backward along the longitudinal axis of the dental handpiece 20 engages the electric motor 60 in respective forward or reverse operation. The switch 70 may be momentary, and may include a potentiometer for variable speed operation of the electric motor 60. The drive shaft 62, which has a threaded portion 64, is coupled to and rotated by the electric motor 60, and is restrained from axial movement.

Figure 2:
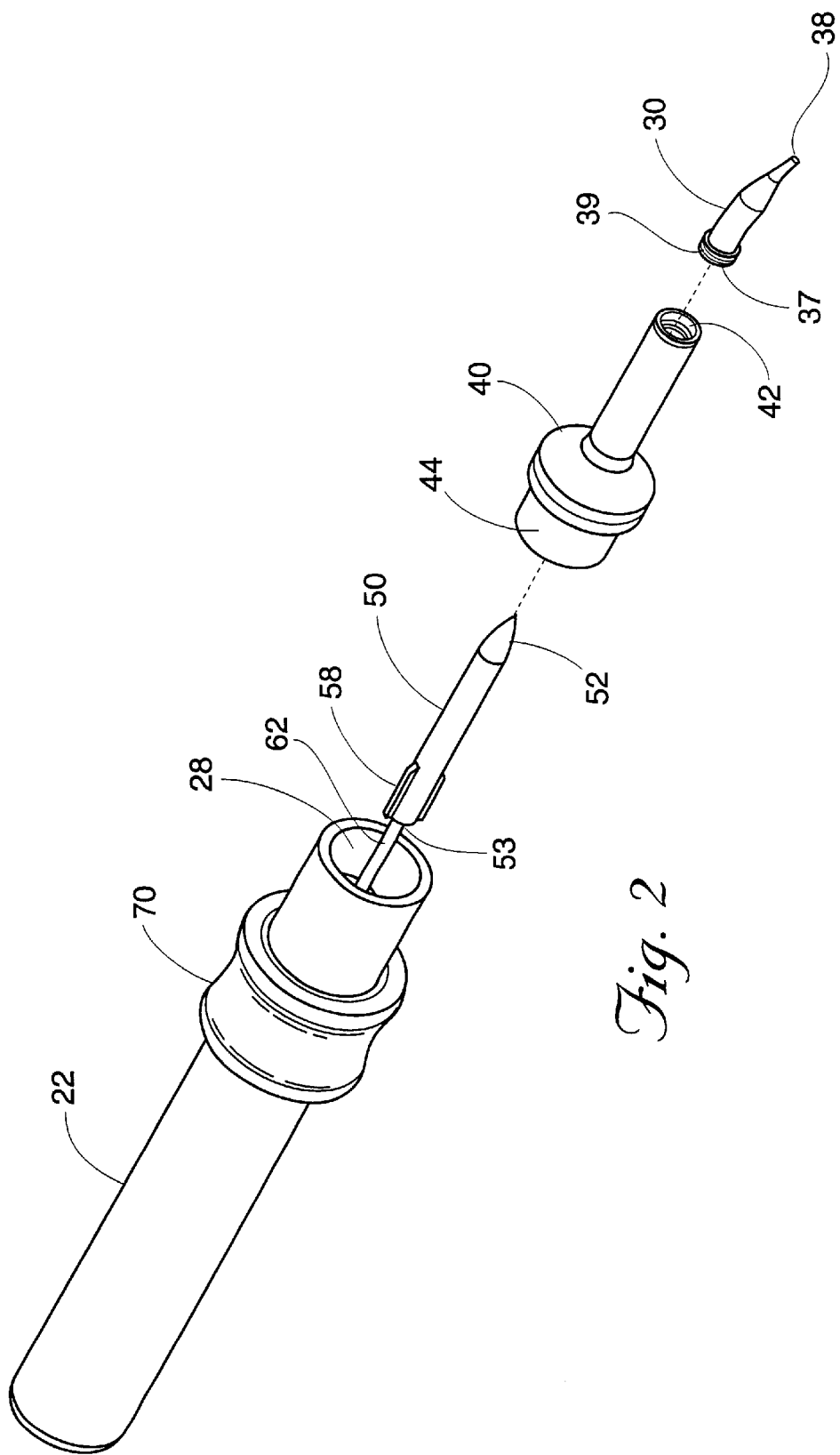
FIG. 2 is a perspective exploded view of the present embodiment of the invention.

With particular reference to FIGS. 2 and 4, the retractable plunger 50 has a hollow internal longitudinal bore 54 beginning at its open end 53 and spanning most of its length. The opposite end is solid and has a cone shaped taper 52. The plunger 50 has an internal threaded portion 56 that engages the threaded length 64 of the drive shaft 62, as illustrated in FIG. 2. The plunger 50 is prevented from rotation with respect to the drive shaft 62 by integrally formed webs 58 that slidably engage longitudinal grooves in the nose cone 40, which remains stationary. As the drive shaft 62 rotates, the plunger 50 advances or retracts longitudinally, depending on the direction of motor 60 and drive shaft 62 rotation. As the plunger 50 advances, it will enter the disposable capsule tip 30, thereby dispensing dental material from the handpiece 20. In the preferred embodiment, the plunger 50 is made of a somewhat flexible material that can bend around curves in the capsule tip 30 and withstand sterilization in high temperatures, such as 135° C. The plunger threaded portion 56 may take the form of a threaded insert molded into the plunger 50, although any method of formation may be used without departing from the present invention.

The nose cone 40 is fastened to the main body 22 with an easily detachable connection. Referring to FIGS. 2 and 4, a receiving opening 28 in the main body 22 is slightly larger than the connecting end 44 of the nose cone 40, allowing a snug fit. A taper may also be designed into the receiving opening 28, connecting end 44, or both, to assure a proper pressure fit connection. It is to be understood that any detachable connecting means may be utilized, such as a push/twist locking action or other conventional design. The front of the nose cone has a threaded interior 42 for receiving the capsule tip 30.

The disposable capsule tip 30 is conventionally available in many variations having a standard size full open end 37 and an array of front opening 38 diameters. A hollow chamber 42 holds the dental material to be dispensed. A flange 39 on the full open end 37 yields as the capsule tip 30 is twisted into the nose cone threaded interior 42, thereby securing the tip 30 to the nose cone 40.

Figure 5:
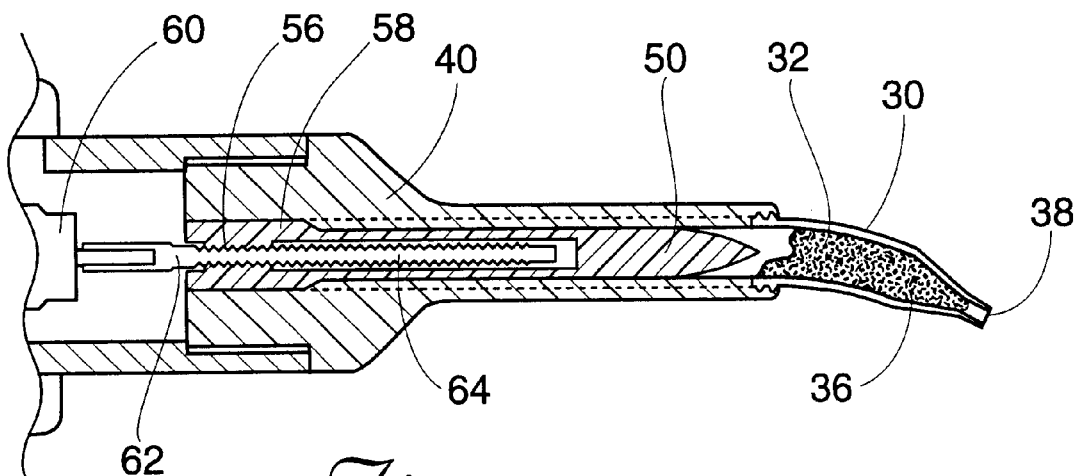
FIG. 5 is a fragmentary longitudinal sectional view depicting the plunger of FIG. 4, positioned in the handpiece, and shown in its starting position.
Figure 6:
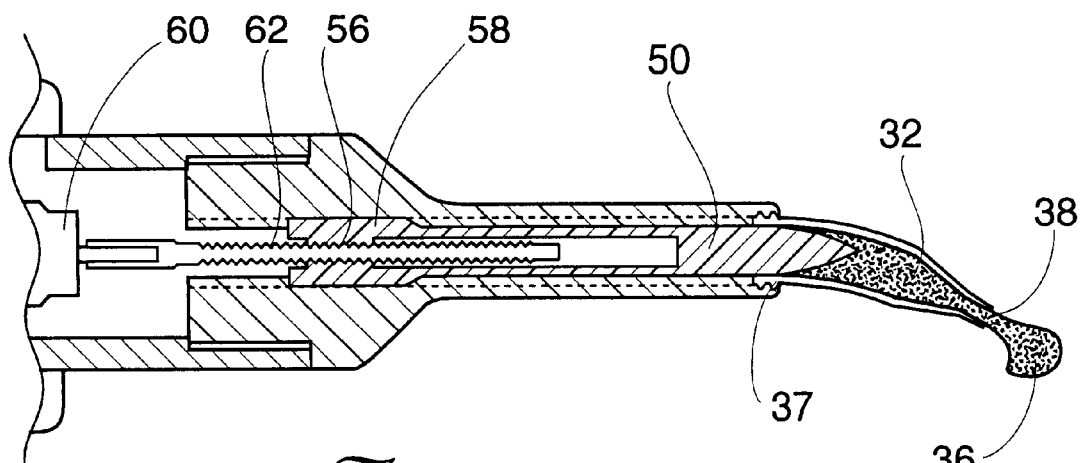
FIG. 6 is a fragmentary longitudinal sectional view depicting the plunger of FIG. 4, shown part way through its travel.
Figure 7:
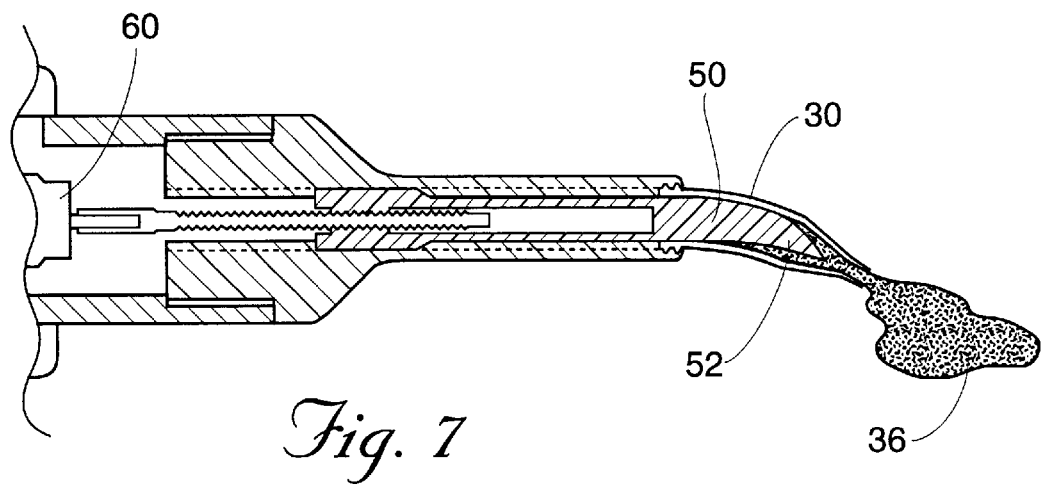
FIG. 7 is a fragmentary longitudinal sectional view depicting the plunger of FIG. 4, shown near the end of its travel.
Figure 8:
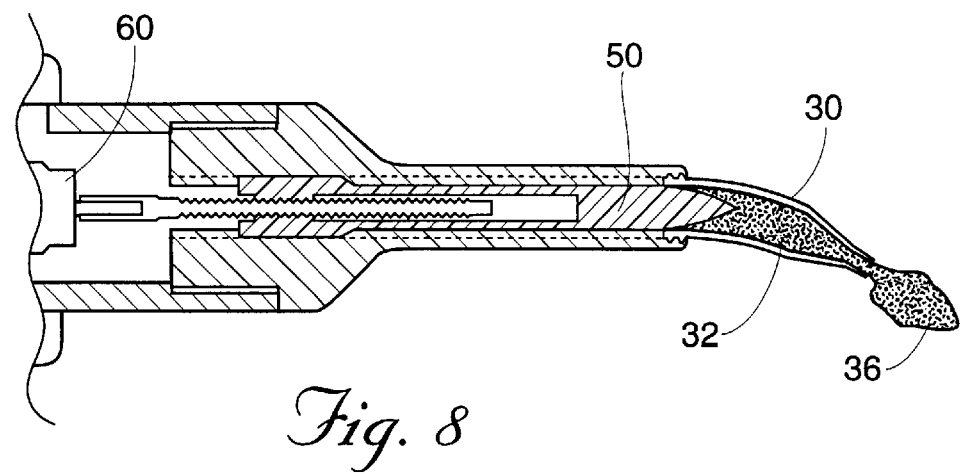
FIG. 8 is a fragmentary longitudinal sectional view depicting the plunger of FIG. 4, shown retracting and recollecting dental material.

FIGS. 5 through 8 illustrate the travel of the plunger 50 and the dispensing of dental material 36. FIG. 5 shows the plunger 50 in the typical rearmost starting position. A disposable capsule tip 30 had been filled with dental material 36 and attached to the nose cone 40. As the electric motor 60 rotates the drive shaft 62, the threaded length 64 of the drive shaft 62 engages the interior threaded portion 56 of the plunger 50, thereby forcing the plunger forward (See FIG. 6). As the plunger 50 enters the internal reservoir 32 of the capsule tip 30, it creates a seal preventing any dental material 36 from escaping through the full open end 37. Dental material 36 is forced out of the capsule tip 30 through the front opening 38. As the plunger 50 extends farther into the internal reservoir 32, it will flex to bend around any curves in the capsule tip 30 (See FIG. 7). The taper 52 and flexibility of the plunger 50 allow all dental material 36 in the capsule tip 30 to be dispensed without using a separate disposable plug. If too much dental material 36 is dispensed, the electric motor 60 can be engaged in reverse, thereby retracting the plunger 50. As the plunger 50 retracts, suction generated in the internal reservoir 32 will draw dental material 36 back into the capsule tip 30.

Figure 9:
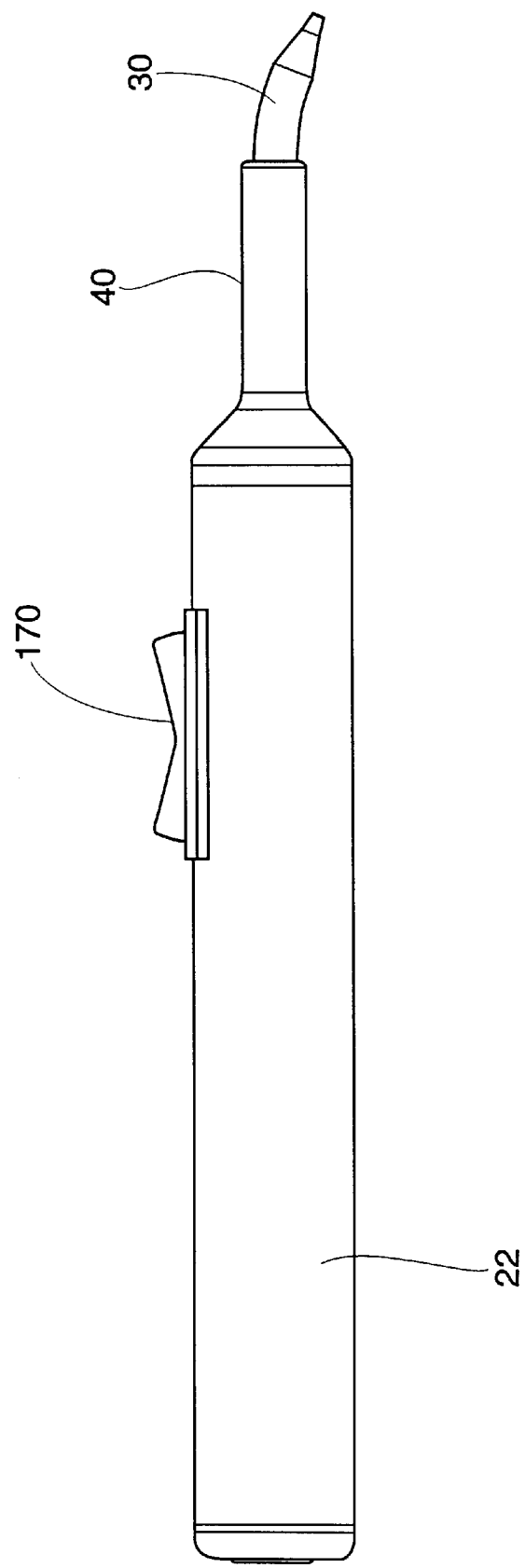
FIG. 9 is a side elevational view of an alternative embodiment of the manually operated power switch of this invention.
Figure 10:
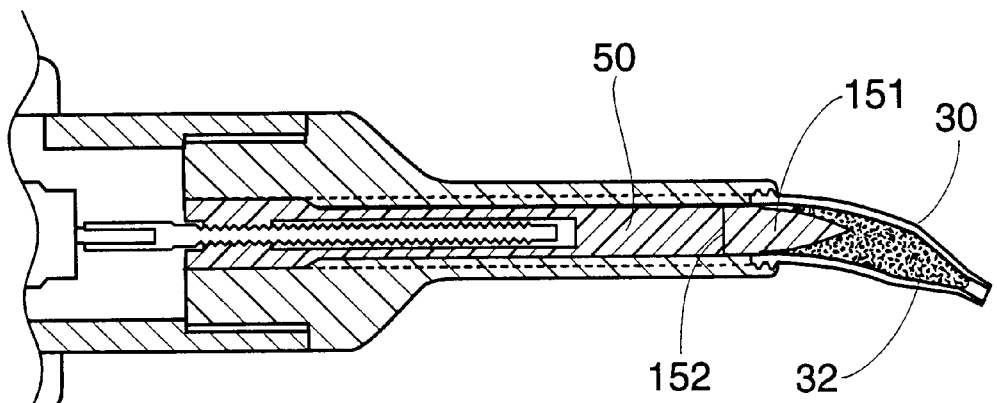
FIG. 10 is a fragmentary longitudinal sectional view of an alternative embodiment of the plunger, shown in its starting position.
Figure 11:
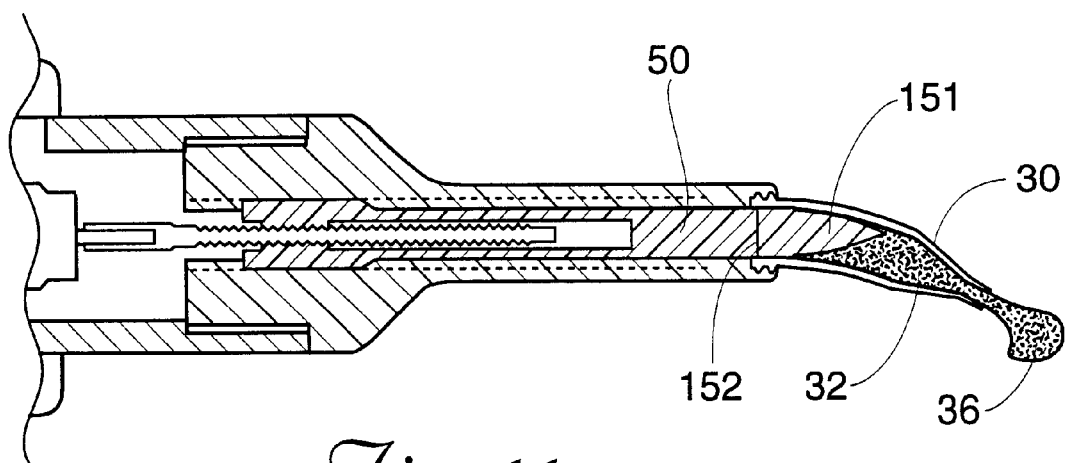
FIG. 11 is a fragmentary longitudinal sectional view of the alternative embodiment of the plunger of FIG. 10, shown part way through its travel.
Figure 12:
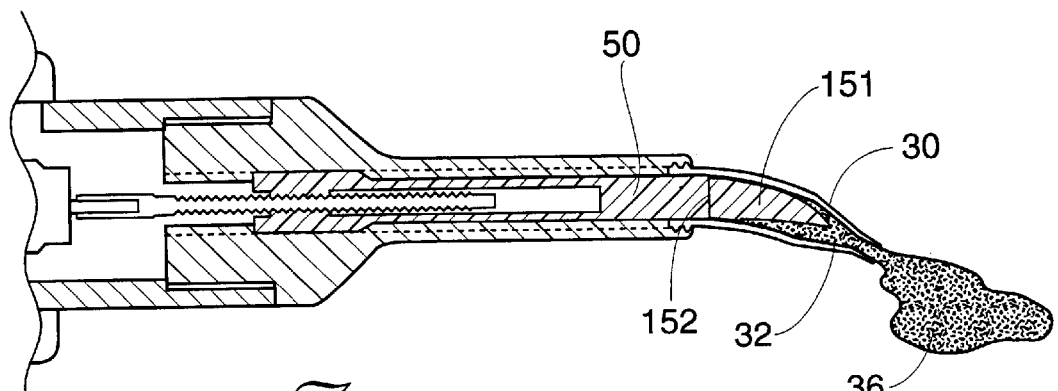
FIG. 12 is a fragmentary longitudinal sectional view of the alternative embodiment of the plunger of FIG. 10, shown near the end of its travel.
Figure 13:
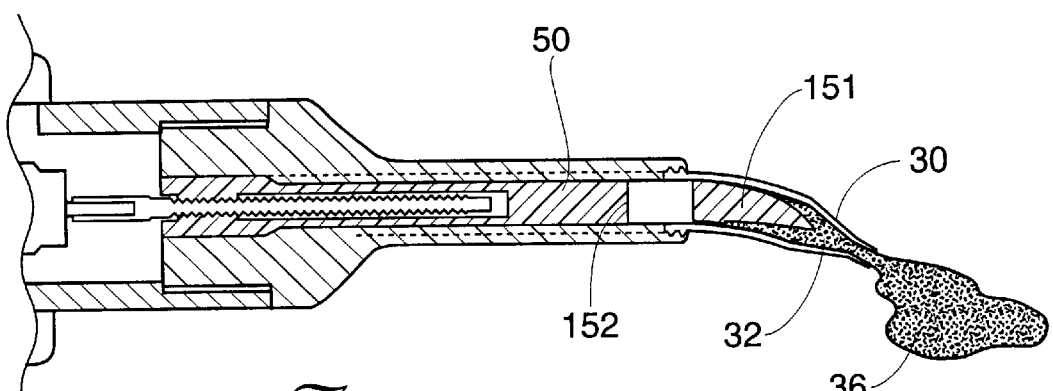
FIG. 13 is a fragmentary longitudinal sectional view of the alternative embodiment of the plunger of FIG. 10, shown in a retracted position.

FIG. 9 shows an alternative embodiment of the present invention, wherein the manual power switch takes the form of a two-way rocker switch 170. Operation and circuitry of the rocker switch 170 may be momentary, and may include a potentiometer in accordance with known practice for variable speed operation of the electric motor 60.

FIGS. 10 through 13 illustrate an alternative embodiment of the present invention, wherein the plunger 50 has a blunt end 152 that pushes a traditional plug 151 into the internal reservoir 32 of the capsule tip 30. This embodiment of the invention is particularly well suited for use with conventionally available capsule tips 30 that are preloaded with dental material 36 and a traditional plug 151. Although the use of a traditional plug 151 prevents the invention from recollecting excess dental material 36, the invention is still superior to conventional dental syringes in the many ways described above.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A dental handpiece arranged for delivery of a composite material, and including a hollow chamber having means for releasable support and communication with a capsule having an internal reservoir for containing said composite material;

said hollow chamber containing:

a reversible electric motor;

a source of electric current arranged to supply electric power to said motor;

a retractable plunger having a hollow internal longitudinal bore, said bore including a threaded portion thereof, said plunger having a forward end communicating with the internal reservoir of said composite-containing capsule and wherein said retractable plunger is flexible for at least a portion of its length, allowing said plunger to substantially conform to the contour of the capsule internal reservoir;

a drive shaft including a threaded drive portion engagable with the threaded portion of said bore of said retractable plunger, said drive shaft being coupled to said electric motor and arranged for reversible rotation by said motor; and a manually operated electric switching means, at least a portion of which is positioned externally of said handpiece chamber and being arranged for controlling electric current for alternative rotational operation of said electrical motor and consequent forward and rearward longitudinal movement of said plunger.

2. The dental handpiece according to claim 1, wherein said source of electric current is a battery enclosed within said hollow chamber.

3. The dental handpiece according to claim 2, wherein said battery is rechargeable.

4. The dental handpiece according to claim 1, wherein said manually operated switching means includes a potentiometer arranged for controlling electric current for variable speed rotational operation of said electrical motor.

* * * * *